US007557141B2

(12) United States Patent
Mishra et al.

(10) Patent No.: US 7,557,141 B2
(45) Date of Patent: Jul. 7, 2009

(54) METHOD OF TREATING AUTOIMMUNE DISEASES

(75) Inventors: Nilamadhab Mishra, Winston-Salem, NC (US); Gary M. Kammer, Lewisville, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 349 days.

(21) Appl. No.: 11/403,608

(22) Filed: Apr. 13, 2006

(65) Prior Publication Data

US 2006/0178437 A1 Aug. 10, 2006

Related U.S. Application Data

(62) Division of application No. 10/187,586, filed on Jul. 2, 2002, now abandoned, which is a division of application No. 09/718,195, filed on Nov. 20, 2000, now abandoned.

(51) Int. Cl.
*A61K 31/185* (2006.01)
(52) U.S. Cl. ..................................... 514/553
(58) Field of Classification Search .................. 514/553
See application file for complete search history.

(56) References Cited

U.S. PATENT DOCUMENTS

| | | | |
|---|---|---|---|
| 4,690,918 | A | 9/1987 | Beppu et al. |
| 5,843,885 | A | 12/1998 | Benedict et al. |
| 5,939,455 | A | 8/1999 | Rephaeli |
| 5,993,845 | A | 11/1999 | Geerts et al. |
| 6,071,923 | A | 6/2000 | Nudelman et al. |
| 6,124,495 | A | 9/2000 | Neiss et al. |
| 6,211,440 | B1 | 4/2001 | Briggs et al. |
| 6,323,334 | B1 | 11/2001 | Kingsbury et al. |
| 6,403,555 | B1 | 6/2002 | Skov |
| 6,544,957 | B2 | 4/2003 | Kern et al. |
| 6,667,341 | B2 | 12/2003 | Lan-Hargest et al. |
| 6,855,515 | B1 | 2/2005 | Rosen et al. |
| 2003/0082666 | A1 | 5/2003 | Kammer et al. |
| 2003/0114525 | A1 | 6/2003 | Kammer |
| 2006/0030626 | A1 | 2/2006 | Kammer |

FOREIGN PATENT DOCUMENTS

| | | |
|---|---|---|
| GB | 2 309 696 A | 8/1997 |
| JP | 07-206670 | 8/1995 |
| WO | WO 93/19778 A1 | 10/1993 |
| WO | WO 97/11366 | 3/1997 |
| WO | WO97/35990 A2 | 10/1997 |
| WO | WO 97/47307 | 12/1997 |
| WO | WO 98/48825 | 11/1998 |
| WO | WO 99/37150 | 7/1999 |
| WO | WO 00/08048 | 2/2000 |
| WO | WO 00/21979 A2 | 4/2000 |
| WO | WO 00/21979 A2 | 4/2000 |
| WO | WO 00/23567 | 4/2000 |

OTHER PUBLICATIONS

Panes et al. "Crohn's Disease . . ." Drugs (2007) 67(17): 2511-2537.*
Strand, V. "Lessons learned from clinical trials in SLE" Autoimmunity Reviews (2007) 6: 209-214.*
Morel, L. (2004) Mouse Models of Human Autoimmune Diseases: Essential Tools That Require the Proper Controls. PLoS Biol 2(8): e24 (pp. 1-31)1; downloaded from http://biology.plosjournals.org/perlserv/?request=get-document&doi=10.1371%2Fjournal.pbio.0020241&ct=1 on Dec. 31, 2008.*
Andrews et al., *Anti-malarial effect of histone deacetylation inhibitors and mammalian tumour cytodifferentiating agents*, International Journal of Parasitology, vol. 30, 2000, pp. 761-768.
Barnes, *Anti-inflammatory actions of glucocorticoids: molecular mechanisms*, Clinical Science, vol. 94, 1998, pp. 557-572.
Berden et al., *Role of Nucleosomes for Induction and Glomerular Binding of Autoantibodies in Lupus Nephritis*, Current Opinion in Nephrology and Hypertension, vol. 8, No. 3, May 1999, pp. 299-306.
Brey et al., *Anti-Intercellular Adhesion Molecule-1 (ICAM-1) antibody treatment prevents central and peripheral nervous system disease in autoimmune-prone mice*, Lupus, vol. 6, 1997, pp. 645-651.
Brosch et al., Abstract, *Inhibition of maize histone deacetylases by HC toxin, the host- selective toxin of Cochliobolus carbonum*, The Plant Cell, vol. 7, 1995, pp. 1941-1950.
Chiurazzi et al., *Synergistic Effect of Histone Hyperacetylation and DNA demethylation in the reactivation of the FMR1 gene*, Human Molecular Genetics, vol. 8, No. 12, 1999, pp. 2317-2323.
Cress et al., *Histone Deacetylases, Transcriptional Control, and Cancer*, Journal of Cellular Physiology, vol. 184, 2000, pp. 1-16.
Dangond et al., *Differential Display Cloning of a Novel Human Histone Deacetylase (HDAC3) cDNA from PHA-Activated Immune Cells*, Biochemical and Biophysical Research Communications, vol. 242, 1998, pp. 648-652.
Darkin-Rattray et al., *Apicidin: A novel antiprotozoal agent that inhibits parasite histone deacetylase*, Proc. Natl. Acad. Sci., USA, vol. 93, Nov. 1996, pp. 13143-13147.
Dayal et al., *The T Cell Enigma in Lupus*, Arthritis & Rheumatism, vol. 39, No. 1, Jan. 1, 1996, pp. 23-33.
Desai-Mehta et al., *Hyperexpresison of CD40 Ligand by B and T Cells in Human Lupus and Its Role in Pathogenic Autoantibody Production*, J. Clin. Invest., vol. 97, No. 9, May 1996, pp. 2063-2073.
Finnin et al., *Structures of a histone deacetylase homologue bound to the TSA and SAHA inhibitors*, Nature, vol. 401, Sep. 9, 1999, pp. 188-193.
Glick et al., PubMed Abstract, *Hybrid polar histone deacetylase inhibitor induces apoptosis and CD95/CD95 ligand expression in human neuroblastoma*, Cancer Res, vol. 59, No. 17, Sep. 1, 1999, pp. 4392-4399.
Guan et al., PubMed Abstract, *Drg-1 as a differentiation-related, putative metastatic suppressor gene in human colon cancer*, Cancer Res, vol. 60, No. 3, Feb. 1, 2000, pp. 749-755.

(Continued)

*Primary Examiner*—Sandra Saucier
*Assistant Examiner*—Susan Hanley
(74) *Attorney, Agent, or Firm*—Myers Bigel Sibley & Sajovec, P.A.

(57) ABSTRACT

A method of treating an autoimmune disease (for example, Systemic Lupus Erythematosus) comprises administering to the subject a treatment effective amount of a histone hyperacetylating agent, or a pharmaceutically acceptable salt thereof. Methods of screening compounds useful for the treatment of autoimmune disease are also disclosed.

2 Claims, 3 Drawing Sheets

OTHER PUBLICATIONS

Horwitz et al., *T Lymphocytes, Natural Killer Cells, Cytokines, and Immune Regulation*, Dubois' Lupus Erythematosus, Wallace et al., eds., (Williams & Wilkins, Baltimore, 1997), pp. 155-194.

Huang et al., *Inhibition of IL-8 Gene Expression in CACO-2 Cells by Compounds Which Induce Histone Hyperacetylation*, Cytokine, vol. 9, No. 1, Jan. 1997, pp. 27-36.

Huggins et al., *Antibodies from systemic lupus erythematosus (SLE) sera define differential release of autoantigens from cell lines undergoing apoptosis*, Clin Exp Immunol, vol. 118, 1999, pp. 322-328.

Kijima et al., *Trapoxin, an Antitumor Cyclic Tetrapeptide, Is an Irreversible Inhibitor of Mammalian Histone Deacetylase*, The Journal of Biological Chemistry, vol. 268, No. 30, Oct. 25, 1993, pp. 22429-22435.

Kim et al., *Ikaros DNA-Binding Proteins Direct Formation of Chromatin Remodeling Complexes in Lymphocytes*, Immunity, vol. 10, Mar. 1999, pp. 345-355.

Kim et al., *PubMed Abstract, Oxamflatin is a novel antitumor compound that inhibits mammalian histone deacetylase*, Oncogene, vol. 18, No. 15, Apr. 15, 1999, pp. 2461-1470.

Kimberley, *Characteristics of Immune Complexes and Principles of Immune Complex Diseases*, Chapter 27, Arthritis and Allied Conditions: A Textbook of Rheumatology, W. J. Koopman, Ed., (Williams & Wilkins, Baltimore, 1997), pp. 529-543.

Kohge et al., *PubMed Abstract, Promotion of antigen-specific antibody production in murine B cells by a moderate increase in histone acetylation*, Biochem Pharmacol, vol. 56, No. 10, Nov. 15, 1998, pp. 1359-1364.

Koipally et al., *Repression by Ikaros and Aiolos is mediated through histone deacetylase complexes*, The EMBO Journal, vol. 18, No. 11, 1999, pp. 3090-3100.

Kornberg et al., *Chromatin-modifying and -remodeling complexes*, Current Opinion in Genetics & Development, vol. 9, 1999, pp. 148-151.

Koshy et al., *Increased Expression of CD40 Ligand on Systemic Lupus Erythematosus Lymphocytes*, J. Clin. Invest, vol. 98, No. 3, Aug. 1996, pp. 826-837.

Kouzarides, *Histone acetylases and deacetylases in cell proliferation*, Current Opinion in Genetics & Development, vol. 9, 1999, pp. 40-48.

Kwon et al., *Depudecin induces morphological reversion of transformed fibroblasts via the inhibition of histone deacetylase*, Proc. Natl. Acad. Sci. USA, vol. 95, Mar. 1998, pp. 3356-3361.

Lea et al., *Discordant effects of butyrate analogues on erythroleukemia cell proliferation, differentiation and histone deacetylase*, Anticancer Res, vol. 15, No. 3, May-Jun. 1995, pp. 879-883.

Lea et al., *PubMed Abstract, Induction of histone acetylation and growth regulation in eryrthroleukemia cells by 4-phenylbutyrate and structural analogs*, Anticancer Res, vol. 19, No. 3A, May-Jun. 1999, pp. 1971-1976.

McBain et al., *Apoptotic Death in Adenocarcinoma Cell Lines Induced by Butyrate and Other Histone Deacetylase Inhibitors*, Biochemical Pharmacology, vol. 53, 1997, pp. 1357-1368.

Nakajima et al., *FR901228, a Potent Antitumor Antibiotic, Is a Novel Histone Deacetylase Inhibitor*, Experimental Cell Research, vol. 241, 1998, pp. 126-133.

Ohno et al., *Macrophage Inflammatory Protein-2: Chromosomal Regulation in Rate Small Intestinal Epithelial Cells*, Proc. Natl. Acad. Sci. USA, vol. 94, Sep. 1997, pp. 10279-10284.

Qiu et al., *Histone Deacetylase Inhibitors Trigger a G2 Checkpoint in Normal Cells That is Defective in Tumor Cells*, Molecular Biology of the Cell, vol. 11, Jun. 2000, pp. 2069-2083.

Richon et al., *A class of hybrid polar inducers of transformed cell differentiation inhibits histone deacetylases*, Proc. Natl. Acad. Sci. USA, vol. 95, Mar. 1998, pp. 3003-3007.

Saito et al., *A synthetic Inhibitor of histone deacetylase, MS-27-275, with marked in vivo antitumor activity against human tumors*, Proc. Natl. Acad. Sci. USA, vol. 96, Apr. 1999, pp. 4592-4597.

Su et al., *Abstract, A Novel Histone Deacetylase Inhibitor Identified by High-Throughput Transcriptional Screening of a Compound Library*, Cancer Research, vol. 60, Jun. 15, 2000, pp. 3137-3142.

Sun et al., *A General Requirement for the Sin3-Rpd3 Histone Deacetylase Complex in Regulating Silencing in Saccharomyces cerevisiae*, Genetics, vol. 152, Jul. 1999, pp. 921-932.

Taunton et al., *A mammalian histone deacetylase related to the yeast transcriptional regulator Rpd3p*, Science, Washington, Apr. 19, 1996.

Taunton et al., *Synthesis of Natural and Modified Trapoxins, Useful Reagents for Exploring Histone Deacetylase Function*, J. Am. Chem. Soc., vol. 118, 1996, pp. 10412-10422.

Wang et al., *PubMed Abstract, Inhibitors of histone deacetylase relieve ETO-mediated repression and induce differentiation of AML1-ETO leukemia cells*, Cancer Res, vol. 59, No. 12, Jun. 15, 1999, pp. 2766-2769.

Yang et al., *Efficacy of a pure compound H1-A extracted from Cordyceps sinensis on autoimmune disease of MRL lpr/lpr mice*, J. Lab. Clin. Med., vol. 134, No. 5, 1999, pp. 492-500.

Yoshida et al., *Potent and Specific Inhibition of Mammalian Histone Deacetylase Both in Vivo and in Vitro by Trichostatin A*, The Journal of Biological Chemistry, vol. 265, No. 28, Oct. 5, 1990, pp. 17174-17179.

Yoshida et al., *PubMed Abstract, Trichostatin and leptomycin. Inhibition of histone deacetylation and signal-dependent nuclear export*, Ann N Y Acad Sci, vol. 886, 1999, pp. 23-36.

Yoshida et al., *Trichostatin A and trapoxin: novel chemical probes for the role of histone acetylation in chromatin structure and function*, BioEssays, vol. 17, No. 5, 1995, pp. 423-430.

Andoh et al. *Sodium butyrate enhances complement-mediated cell injury via down-regulation of decay-accelerating factor expression in colonic cancer cells*, Cancer Immunology Immunotherapy, vol. 50, 2002, pp. 663-672.

Nancey et al. *Butyrate strongly inhibits in vitro stimulated release of cytokines in blood*, Digestive Diseases and Sciences, vol. 47, No. 4, 2002, pp. 921-928.

Saemann et al. *Anti-inflammatory effects of sodium butyrate on human monocytes: potent inhibition of IL-12 and up-regulation of IL-10 production*, The FASEB Journal, vol. 14, 2000, pp. 2380-2382.

Sugimoto et al. *Effects of a new anti-rheumatic drug KE-298 and its active metabolite: KE-758 on secretion of thioredoxin and on the level of intracellular glutathione in human monocytes and T cells*, Molecular Immunology, vol. 38, 2001, pp. 793-799.

International Search Report, PCT/US01/43871, Sep. 18, 2002.

Dangond et al. "Differential expression of human histone deacetylase mRNAs in response to immune cell apoptosis induction by Trichostatin A and Butyrate" Biochem. Biophys. Res. Comm. (1998) 247: 833-837.

Taber's Medical Dictionary, 15th edition, 1981 (F.A. Davis Company: Philadelphia, PA) p. 982.

Kohge et al. "Promotion of antigen-specific antibody production in murine B cells by a moderate increase in histone acetylation" Biochem. Pharmacol. (1998) 56: 1359-1364.

English Machine Translation of JP 07206670 from JAPIO website.

Application from related application (filing receipt attached). Kammer et al., *Method of Treating Autoimmune Disease*, U.S. Appl. No. 09/718,195, filed Nov. 20, 2000.

Reilly et al. "Modulation of Renal Disease in MRL/*lpr* Mice by Suberoylanilide Hydroxamic Acid" *The Journal of Immunology* 173:4171-4178 (2004).

* cited by examiner

METHOD OF TREATING AUTOIMMUNE DISEASES

CROSS-REFERENCE TO RELATED APPLICATION

The present application is a divisional of U.S. patent application Ser. No. 10/187,586, filed Jul. 2, 2002, which is a divisional of U.S. patent application Ser. No. 09/718,195, filed Nov. 20, 2000 (now abandoned), the disclosures of which are incorporated herein by reference in their entireties.

STATEMENT OF FEDERAL SUPPORT

This invention was made possible with government support under grant numbers R01 AR39501 from the National Institute of Health. The United States government has certain rights to this invention.

FIELD OF THE INVENTION

The present invention relates to methods for the treatment of autoimmune diseases such as systemic lupus erythematosus.

BACKGROUND OF THE INVENTION

The hallmark of the aberrant cellular immune response in systemic lupus erythematosus (SLE) is T cell dysfunction (A. K. Dayal and G. M. Kammer, *Arthritis Rheum.* 39, 23 (1996); D. A. Horwitz, et al., in *Dubois' Lupus Erythematosus.*, D. J. Wallace and B. H. Hahn, Eds. (Williams & Wilkins, Baltimore, 1997), chap. 10). An imbalance exists between exaggerated helper function and deficient cytotoxic/suppressor activity that promotes inappropriate B cell overproduction of immunoglobulins (Ig). The resulting polyclonal hypergammaglobulinemia is comprised of natural antibodies and pathogenic autoantibodies, including anti-native DNA. Formation of complement-fixing immune complexes in situ or their deposition on vascular endothelium, such as the renal glomerulus, initiates a chronic inflammatory response that leads to irreparable parenchymal damage, ultimately resulting in end-organ failure (R. P. Kimberly, in *Arthritis and Allied Conditions: A Textbook of Rheumatology*, W. J. Koopman, Ed. (Williams & Wilkins, Baltimore, 1997), chap. 27). Moreover, T cell dysfunctions predispose to recurrent, often life-threatening infections (A. G. Iliopoulos and G. C. Tsokos, *Sem. Arthritis Rheum.* 25, 318 (1996); C. A. Hunter and S. L. Reiner, *Curr. Opin. Immunol.* 12, 413 (2000)).

Two principal defects of T cell function in SLE are augmented expression of cell surface receptors and altered production of cytokines. CD40 ligand (CD154) expression is significantly increased and prolonged on both $CD4^+$ helper (Th) and $CD8^+$ cytotoxic/suppressor (Tc) subpopulations (M. Koshy, et al., *J. Clin. Invest.* 98, 826 (1996); A. Desai-Mehta, et al, *J. Clin. Invest.* 97, 2063 (1996)). This prolonged overexpression may be pathophysiologically significant, for binding of CD154 on Th cells to CD40 on B cells promotes B cell activation and may drive the polyclonal hypergammaglobulinemia. Moreover, Th2 cells over-produce IL-10 whereas Th1 cells under-produce IFN-γ. Heightened levels of IL-10 may profoundly modify the cellular immune response by (a) downregulating both IFN-γ and IL-2 production by Th1 cells; (b) inhibiting IL-12 generation and down-regulating expression of IL-12 receptors on Th1 cells; (c) up-regulating bcl-2 expression and preventing apoptosis of activated T cells; and, (d) promoting B cell growth, differentiation and autoantibody production. By contrast, deficient IFN-γ may significantly hinder cellular immunity in SLE by both impairing Tc-dependent cytotoxicity and altering antigen-presentation (B. S. Handwerger, et al., in *Lupus: Molecular and Cellular Pathogenesis*, G. M. Kammer and G. C. Tsokos, Eds. (Humana Press, Totowa, N.J., 1999), chap. 21).

While several treatments for SLE and other autoimmune diseases have been developed, none are entirely satisfactory. Hence, there remains a need for new ways to treat autoimmune diseases such as SLE.

SUMMARY OF THE INVENTION

A first aspect of the present invention is a method of treating an autoimmune disease in a subject in need thereof, comprising administering to the subject a treatment effective amount of a histone hyperacetylating agent, or a pharmaceutically acceptable salt thereof.

A second aspect of the present invention is a method of treating Systemic Lupus Erythematosus in a subject in need thereof, comprising administering to that subject a treatment effective amount of a histone hyperacetylating agent, or a pharmaceutically acceptable salt thereof.

A still further aspect of the present invention is the use of an active agent as described above for the preparation of a medicament for the treatment of a disorder as described above.

Still further aspects of the present invention are methods of screening candidate compounds for activity in treating autoimmune diseases such as systemic lupus erythematosus.

Histone deacetylases (HDACs) are enzymes that deacetylate specific lysine residues of histone amino-terminal tail domains and certain non-histone substrates. Current evidence implicates the deacetylases in transcriptional repression (T. Kouzarides, *Curr. Opin. Genet. Dev.* 9, 40 (1999); W. D. Cress and E. Seto, *J. Cell. Physiol.* 184, 1 (2000)). Complexed with Sin3 and Mi2 transcriptional co-repressor proteins, HDAC/Sin3 and HDAC/Mi2 associate with other DNA-binding proteins, such as Ikaros (W. D. Cress and E. Seto, *J. Cell. Physiol.* 184, 1 (2000); J. Kim et al., *Immunity* 10, 345 (1999)). These deacetylase complexes appear to limit the accessibility of transcription factors to the promoter by closely juxtaposing the nucleosome to DNA. Of the eight human HDACs discovered (W. D. Cress and E. Seto, *J. Cell. Physiol.* 184, 1 (2000)), to date only HDACs1-3 have been identified in T cells (F. Dangond et al., *Biochem. Biophys. Res. Comm.* 242, 648 (1998)). During T cell activation, HDAC/Mi2 complexes are recruited to regions of the heterochromatin by Ikaros and modulate gene expression (J. Kim et al., *Immunity* 10, 345 (1999); Koipally, J., et al. *EMBO J.* 18, 3090 (1999)). Trichostatin A, an HDAC inhibitor (M. Yoshida, et al., *J. Biol. Chem.* 265, 17174 (1990); S. Finnin et al., *Nature* 401, 188 (1999)), blocks deacetylase activity and shifts the equilibrium toward histone acetylation. By acetylating histones, chromatin is remodeled, promoting access of DNA-binding transcription factors and the transcriptional machinery to promoter/enhancer regions (W. D. Cress and E. Seto, *J. Cell. Physiol.* 184, 1 (2000); R. D. Kornberg and Y. Lorch, *Curr. Opin. Gen. Dev.* 9, 148 (1999)). Acetylation may mediate positive or negative regulatory events that depend upon the particular gene (Z. W. Sun and M. Hampsey, *Genetics* 152, 921 (1999)). Thus, promoter regions that are ordinarily silenced can then be derepressed whereas those that are expressed can be repressed. However, the use of histone deacetylase inhibitors or other histone hyperacetylating agents in the treatment of autoimmune diseases such as SLE has not heretofore been suggested or disclosed.

DETAILED DESCRIPTION OF PREFERRED EMBODIMENTS

Figure 1:
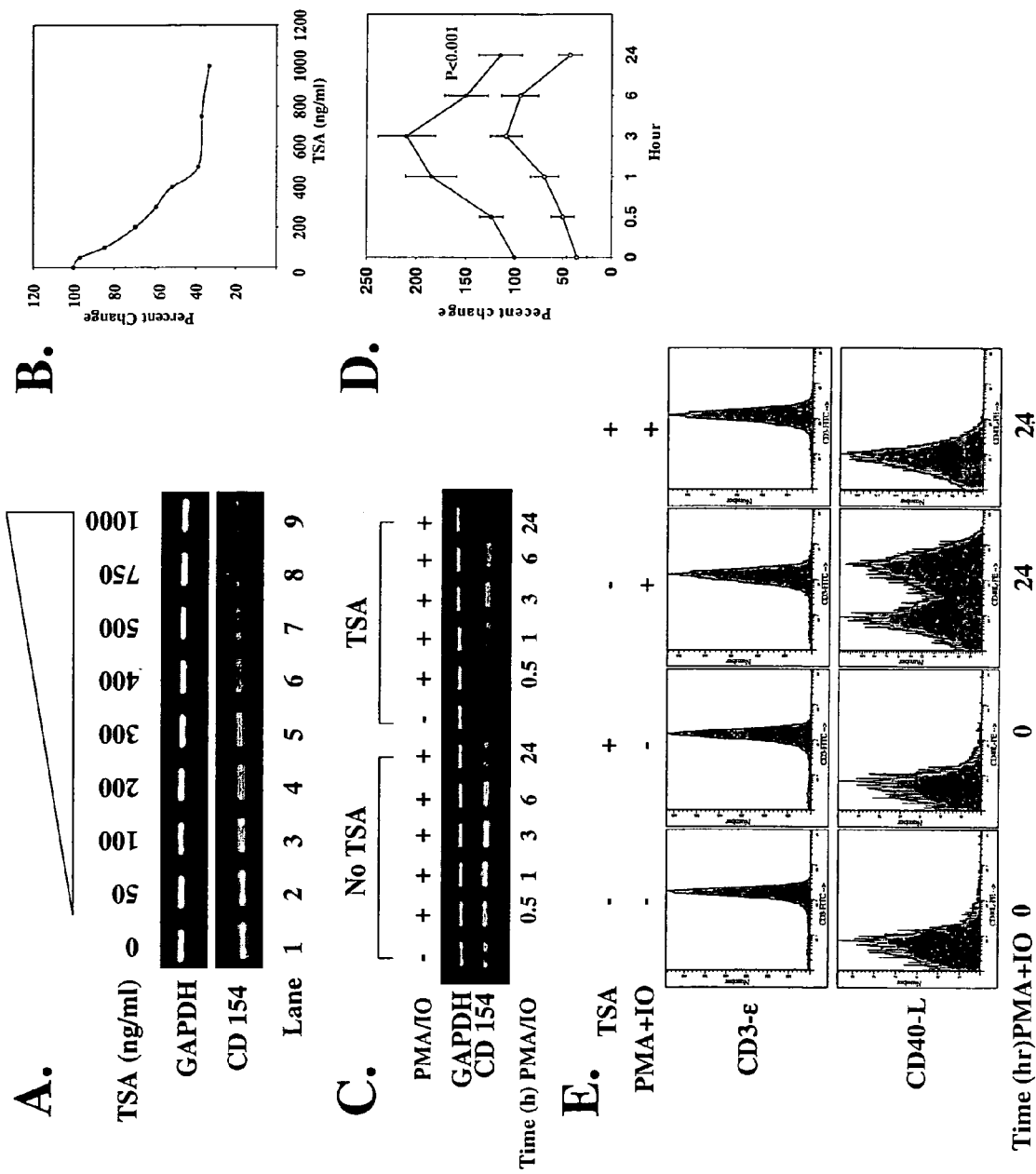
FIG. 1A shows the down-regulation of CD154 transcript levels by TSA. Increasing concentrations of TSA (0-1000 ng/ml) progressively inhibit expression of CD154 mRNA relative to expression of GAPDH mRNA.
FIG. 1B shows a graphic depiction of a densitometric scan of the gel in FIG. 1A. This graph depicts the percent change of CD154 mRNA expression with increasing concentrations of TSA over 24 hr. GAPDH mRNA expression is stable and unchanged in the presence of TSA.
FIG. 1C shows CD154 transcript levels in T cells incubated in the absence or presence of 1000 ng/ml TSA over 18 hr. T cells were then stimulated with 20 ng/ml PMA+0.5 µM IO for intervals to 24 hr. CD154 mRNA expression relative to GAPDH mRNA expression is shown.
FIG. 1D shows a graphic depiction of the percent change in CD154 mRNA expression over time in the absence (filled circles) or presence (open circles) of TSA.
FIG. 1E shows flow cytometric analysis of CD154 and CD3-ε expression on SLE T cells. T cells were cultured in the absence or presence of 1000 ng/ml TSA for 18 hr, and subsequently activated with 20 ng/ml PMA+0.5 µM IO for 24 hr. The abscissa denotes the number of cells and ordinate the intensity of cell fluorescence signal. Statistical analyses were performed by paired Student's t test or one-way ANOVA.

The term "treat" as used herein refers to any type of treatment that imparts a benefit to a patient afflicted with a disease, including improvement in the condition of the patient (e.g., in one or more symptoms), delay in the progression of the disease, etc.

The term "pharmaceutically acceptable" as used herein means that the compound or composition is suitable for administration to a subject to achieve the treatments described herein, without unduly deleterious side effects in light of the severity of the disease and necessity of the treatment.

Active compounds of the present invention may optionally be administered in conjunction with other compounds useful in the treatment of the autoimmune disease such as SLE. The other compounds may optionally be administered concurrently. As used herein, the word "concurrently" means sufficiently close in time to produce a combined effect (that is, concurrently may be simultaneously, or it may be two or more events occurring within a short time period before or after each other).

As used herein, the administration of two or more compounds "concurrently" or "in combination" means that the two compounds are administered closely enough in time that the presence of one alters the biological effects of the other. The two compounds may be administered simultaneously or sequentially. Simultaneous administration may be carried out by mixing the compounds prior to administration, or by administering the compounds at the same point in time but at different anatomic sites or using different routes of administration.

Autoimmune diseases with which the present invention is concerned include, but are not limited to, Rheumatoid Arthritis, Sjogren's disease, Polymyositis, Dermatomyositis, and Systemic Lupus Erythomatosus. A particularly preferred application of the present invention is in the treatment of Systemic Lupus erythomatosus (SLE).

The present invention is primarily concerned with the treatment of human subjects, but the invention may also be carried out on animal subjects, particularly mammalian subjects such as mice, rats, dogs, cats, livestock and horses for veterinary purposes, and for drug screening and drug development purposes. In addition, the present invention may be used to treat animal subjects that are models of an autoimmune disease for drug screening and development purposes. A particular example of such a model is the mouse NZB/NZW F1 model of SLE.

1. Active Compounds.

Active compounds used to carry out the present invention are, in general, histone hyperacetylating agents, such as histone deacetylase inhibitors. Numerous such compounds are known. See, e.g., P. Dulski, Histone Deacetylase as Target for Antiprotozoal Agents, PCT Application WO 97/11366 (27 Mar. 1997). Examples of such compounds include, but are not limited to:

A. Trichostatin A and its analogues, such as: Trichostatin A (TSA); and Trichostatin C (Koghe et al. 1998. *Biochem. Pharmacol.* 56:1359-1364) (Trichostatin B has been isolated but not shown to be an HDAC inhibitor).

B. Peptides, such as: Oxamflati [(2E)-5-[3-[(phenylsufonyl)aminol phenyl1]-pent-2-en-4-ynohydroxamic acid (Kim et al. *Oncogene*, 18:2461-2470 (1999)); Trapoxin A (TPX)—Cyclic Tetrapeptide (cyclo-(L-phenylalanyl-L-phenylalanyl-D-pipecolinyl-L-2-amino-8-oxo-9,10- epoxy-decanoyl)) (Kijima et al., *J. Biol. Chem.* 268, 22429-22435 (1993)); FR901228, Depsipeptide (Nakajima et al., *Ex. Cell Res.* 241, 126-133 (1998)); FR225497, Cyclic Tetrapeptide (H. Mori et al., PCT Application WO 00/08048 (17 Feb. 2000)); Apicidin, Cyclic Tetrapeptide [cyclo(N-O-methyl-L-tryptophanyl-L-isoleucinyl-D-pipecolinyl-L-2-amino-8-oxodecanoyl)] (Darkin-Rattray et al., *Proc. Natl. Acad. Sci. USA* 93, 13143-13147 (1996)); Apicidin Ia, Apicidin Ib, Apicidin Ic, Apicidin IIa, and Apicidin IIb (P. Dulski et al., PCT Application WO 97/11366); HC-Toxin, Cyclic Tetrapeptide (Bosch et al., *Plant Cell* 7, 1941-1950 (1995)); WF27082, Cyclic Tetrapeptide (PCT Application WO 98/48825); and chlamydocin (Bosch et al., supra).

C. Hydroxamic Acid-Based Hybrid Polar Compounds (HPCs), such as: Salicylihydroxamic Acid (SBHA) (Andrews et al., *International J. Parasitology* 30, 761-768 (2000)); Suberoylanilide Hydroxamic Acid (SAHA) (Richon et al., *Proc. Natl. Acad. Sci. USA* 95, 3003-3007 (1998)); Azelaic Bishydroxamic Acid (ABHA) (Andrews et al., supra); Azelaic-1-Hydroxamate-9-Anilide (AAHA) (Qiu et al., *Mol. Biol. Cell* 11, 2069-2083 (2000)); M-Carboxycinnamic Acid Bishydroxamide (CBHA) (Ricon et al., supra); 6-(3-Chlorophenylureido)carpoic Hydroxamic Acid (3-Cl-UCHA) (Richon et al., supra); MW2796 (Andrews et al., supra); and MW2996 (Andrews et al., supra). Note that analogs not effective as HDAC Inhibitors are: Hexamethylene bisacetamide (HBMA) (Richon et al. 1998, PNAS, 95:3003-3007); and Diethyl bix(pentamethylene-N,N-dimethylcarboxamide) malonate (EMBA) (Richon et al. 1998, PNAS, 95:3003-3007).

D. Short Chain Fatty Acid (SCFA) Compounds, such as: Sodium Butyrate (Cousens et al., *J. Biol. Chem.* 254, 1716-1723 (1979)); Isovalerate (McBain et al., *Biochem. Pharm.* 53:1357-1368 (1997)); Valerate (McBain et al., supra); 4-Phenylbutyrate (4-PBA) (Lea and Tulsyan, *Anticancer Research,* 15, 879-873 (1995)); Phenylbutyrate (PB) (Wang et al., *Cancer Research,* 59, 2766-2799 (1999)); Propionate (McBain et al., supra); Butrymide (Lea and Tulsyan, supra); Isobutyramide (Lea and Tulsyan, supra); Phenylacetate (Lea and Tulsyan, supra); 3-Bromopropionate (Lea and Tulsyan, supra); and Tributyrin (Guan et al., *Cancer Research,* 60, 749-755 (2000)).

E. Benzamide derivatives, such as: MS-27-275 [N-(2-aminophenyl)-4-[N-(pyridin-3-yl-methoxycarbonyl)aminomethyl]benzamide] (Saito et al., *Proc. Natl. Acad. Sci. USA* 96, 4592-4597 (1999)); and 3'-amino derivative of MS-27-275 (Saito et al., supra).

F. Other inhibitors, such as: Depudecin [its analogues (mono-MTM-depudecin and depudecin-bisether) do not inhibit HDAC) (Kwon et al. 1998. PNAS 95:3356-3361); and Scriptaid (Su et al. 2000 Cancer Research, 60:3137-3142).

The active compounds disclosed can, as noted above, be prepared in the form of their pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

2. Compounds for Concurrent Administration.

The active compound histone hyperacetylating agents described herein may be administered concurrently with other active compounds known for the treatment of autoimmune diseases (such as systemic lupus erythematosus). Examples of such other active compounds include, but are not limited to: (i) corticosteroids such as prednisolone sodium phosphate, such as Pediapred®; methylprednisolone, such as Medrol®; prednisone, such as Deltasone®) or Orasone®; and dexamethasone, such as Decadron® Tablets; (ii) steroids such as lynestrenol—a progestagen; desogestrel—a progestagen; ethylestrenol—an anabolic steroid; and tibolone—a weak progestational, anabolic, androgenic steroid (H. A. Verheul et al. *Clin. Immunol. Immunopathol.* 38:198-208 (1986)); and exogenous DHEA—dihydroepiandosterone—(T. Suzuki et al. *Clin. Exp. Immunol.* 99:251-255 (1995)); and (iii) other compounds such as hydroxchloroquine sulfate, such as Plaquenil®); H1-A (isolated from Cordyceps sinensis) (L. Y. Yang, et al. *J. Lab Clin. Med.* 134:492-500 (1999)); sulfasalazine (a.k.a. Salazosulfapyridine) (E. Delaporte et al. *Ann. Dermatol. Venereol.* 124:151-156 (1997)); anti-ICAM-1—murine antiintercellular adhesion molecule-1 (R. L. Brey et al. *Lupus* 6:645-651 (1997)); MX-68—upolyglutamable antifolate (M. Mihara et al. *Int. Arch. Allergy Immunol.* 13:454-459 (1997)); FK506—(K. Yamamoto et al. *Immunology* 69:222-227 (1990)); AS 101—organotellurium compound—(J. Alcocer-Varela et al. *Clin. Exp. Immunol.* 77:319-323 (1989)); HWA-131-(3—(3,5-ditert.butyl-4-hydroxyphenyl)-7H-thiazolo(3,2-b)(1,2,4)triazin-7-one) (R. R. Bartlett et al. *Drugs Exp. Clin. Res.* 15:521-526 (1989)); and Auranofin—Oral gold compound—(K. Dalziel et al. *Br. J. Dermatol.* 115:211-216 (1986)).

The foregoing may be administered in the same formulation and/or by the same route of administration, or by a different formulation and/or different route of administration, as the active agent histone hyperacetylating agents described herein, in their conventional dosages or dosages which can be determined from the conventional dosages.

3. Pharmaceutical Formulations.

The active compounds described above may be formulated for administration in a pharmaceutical carrier in accordance with known techniques. See, e.g., Remington, *The Science And Practice of Pharmacy* ($9^{th}$ Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well known techniques of pharmacy consisting essentially of admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, intraperitoneal, intravenous, etc.), topical (e.g., both skin and mucosal surfaces, including airway surfaces) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound, which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising an active compound as described above, or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis\tris buffer (pH 6) or ethanol/water and contain from 0.1 to 0.2M active ingredient.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds disclosed herein or salts thereof, may be lyophilized to produce a lyophilizate which may be reconstituted with a pharmaceutically acceptable carrier, such as water, to regenerate a liposomal suspension.

Other pharmaceutical compositions may be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

In addition to active compounds or their salts, the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

4. Dosage and Routes of Administration.

As noted above, the present invention provides pharmaceutical formulations comprising the active compounds (including the pharmaceutically acceptable salts thereof), in pharmaceutically acceptable carriers for oral, rectal, topical, buccal, parenteral, intramuscular, intradermal, or intravenous, and transdermal administration.

The therapeutically effective dosage of any specific compound, the use of which is in the scope of present invention, will vary from compound to compound and patient to patient, and will depend upon factors such as the age, weight, and condition of the patient and the route of delivery. As a general proposition, a dosage from about 0.01 or 0.1 to about 50, 100 or 500 mg/kg will have therapeutic efficacy, with all weights being calculated based upon the weight of the active compound, including the cases where a salt is employed. Toxicity concerns at the higher level may restrict intravenous dosages to a lower level such as up to about 10 mg/kg, with all weights being calculated based upon the weight of the active base, including the cases where a salt is employed. A dosage from about 10 mg/kg to about 50 mg/kg may be employed for oral administration. Typically, a dosage from about 0.5 mg/kg to 5 mg/kg may be employed for intramuscular injection. Preferred dosages are 1 μmol/kg to 50 μmol/kg, and more preferably 22 μmol/kg and 33 μmol/kg of the compound for intravenous or oral administration. The duration of the treatment is usually once per day for a period of two to three weeks or until the condition is essentially controlled. Lower doses given less frequently can be used prophylactically to prevent or reduce the incidence of recurrence of the disorder, or the severity of symptoms. For example, the trichostatin analog SAHA is being given in phase I clinical trials for cancer by an intraveneous route.

5. Screening Assays.

The present invention also provides screening assays for identifying compounds useful, or potentially useful, in the treatment of autoimmune diseases such as SLE. Such assays may be carried out in accordance with known techniques, such as the formats described in P. Dulski, PCT Application WO97/11366 (27 Mar. 1997).

One method of screening compounds for activity in treating an autoimmune disease, comprises
  (a) contacting a histone deacetylase, or an extract containing histone deacetylase with (i) a known amount of a labeled compound that interacts with a histone deacetylase; and (ii) a known dilution of a test compound or natural product extract; and then
  (b) determining the inhibition of interaction of said labeled compound with said histone deacetylase induced by said test compound, where the inhibition of interaction of said labeled compound with said histone eacetylase indicates said compound or extract is a candidate for the treatment of an autoimmune disease.

The histone deacetylase is preferably a mammalian (e.g., mouse, rat, rabbit) histone deacetylase, and is most preferably a human histone deacetylase. The labeled compound may be any of the active agents described above, labeled with a suitable detectable group such as tritium. In general, the labeled compound will be one which binds to histone deacetylase or is a substrate of histone deacetylase. The test compound may be of any source, such as an oligomer or a non-oligomer from a combinatorial library, or a rationally synthesized candidate compound. Extracts may be obtained from any suitable source, such as plant extracts obtained through techniques known in traditional, folk or herbal medicine. The determining step may be carried out qualitatively or quantitatively by any suitable means, such as by Scatchard analysis with a series of serial dilutions of the test compound or extract.

In another embodiment, a method of screening compounds for activity in treating an autoimmune disease such as SLE comprises:
  (a) contacting an intact host cell in vivo or in vitro with a test compound or a natural product extract; and then
  (b) determining the level of histone acetylation in said cell, wherein elevated levels of histone acetylation indicates said compound or extract is a candidate for the treatment of an autoimmune disease.

Where the contacting step is carried out in vivo (e.g., as in the course of a clinical trial) the compound is administered to a suitable subject carrying the cell by any of the same techniques described above for administering active agents, and the cell (or collection of cells) subsequently collected from the subject for use in the determining step. The cell (or subject) is preferably mammalian (e.g., a mouse, rat or rabbit cell) and in one particularly preferred embodiment is human. Lymphocytes are particularly preferred cells. The subject may be one afflicted with an autoimmune disease such as SLE (including models of such a disease), or may be a normal (or unafflicted) subject. Elevated levels may be determined by comparison to an untreated, control subject or cell, by comparison to levels found in the the same subject or cell or cell population prior to treatment, etc. Assays for histone levels may be carried out by any suitable technique, with histone level assays being known to those skilled in the art.

The examples, which follow, are set forth to illustrate the present invention, and are not to be construed as limiting thereof. In the following examples, hr means hour; min means minute; TSA means Trichostatin A; SLE means systemic lupus erythematosus; RT-PCR means reverse transcriptase polymerase chain reaction; IO means ionomycin, PMA means phorbol myristate acetate, ml means milliliter; ng means nanogram; and all temperatures, unless otherwise indicated, are in degrees Celsius.

EXAMPLE 1

Down-Regulation of CD154 Transcript and Protein Levels by TSA

Because SLE T cells are often activated (D. T. Y. Yu et al., *J. Exp. Med.* 151, 91 (1980).), the up-regulation of CD154 and IL-10 and down-regulation of IFN-γ may reflect skewed gene expression due to enhanced recruitment of HDACs to the promoters of these genes. The resulting dysequilibrium of acetylation might be expected to alter the chromatin structure of the promoters (R. D. Kornberg and Y. Lorch, *Curr. Opin. Gen. Dev.* 9, 148 (1999)), thereby activating previously silenced genes while repressing expressed genes. To determine if TSA can down-regulate CD154 transcript expression, T cells from eight SLE subjects were treated with increasing concentrations of TSA over 18 hr.

T cells were cultured in the absence or presence of increasing concentrations of TSA for 18 hr in 5% $CO_2$ at 37° C. RNA was isolated, cDNAs were prepared, and RT-PCR was performed as previously detailed (D. Laxminarayana, et al., *J. Clin. Invest.* 92, 2207 (1993)). The primers used were:

```
CD154:
5'-GAATCCTCAAATTGCGGCAC-3'        (SEQ ID NO:1)
and
5'-CAGAAGGTGACTTGGCATAG-3';       (SEQ ID NO:2)

GAPDH:
5'-GGTGAAGGTCGGAGTCAACG-3'        (SEQ ID NO:3)
and
5'-CAAAGTTGTCATGGATGACC-3';       (SEQ ID NO:4)

IL-10:
5'-TTGCCTGGTCCTCCTGACTG-3'        (SEQ ID NO:5)
and
5'-GATGTCTGGGTCTTGGTTCT-3';       (SEQ ID NO:6)

IFN-γ:
5'-ATGAAATATACAAGTTATATCTTGGCTTT-3'  (SEQ ID NO:7)
and
5'-GATGCTCTTCGACCTCGAAACAGCAT-3'.    (SEQ ID NO:8)
```

The reaction mixtures were subjected to 30 cycles of denaturation (94° C., 1 min) and annealing for 1 min at 53° C. (CD154), 40° C. (GAPDH) and 55° C. (IL-10 and IFN-γ). Extension was for 2 min at 72° C. with a final extension of 7 min at 72° C. using a DNA thermal cycler (Perkin-Elmer).

FIGS. 1A and 1B demonstrate that TSA maximally inhibits CD154 transcript by 60%, but does not modify GAPDH mRNA expression. When SLE T cells were activated with phorbol myristate acetate (PMA) and ionomycin (IO), CD154 mRNA content increased 100%, peaked at 3 hr, and waned thereafter (FIGS. 1C and 1D). Under these conditions, however, GAPDH mRNA remained stable, demonstrating that cellular activation also does not modify the expression of this gene. By contrast, when T cells were preincubated with TSA for 18 hr and then activated by PMA+IO over intervals to 24 hr, up-regulation of CD154 transcript was significantly reduced throughout the entire time course compared to cells not exposed to TSA (FIGS. 1C and 1D; P<0.001). Thus, in SLE T cells TSA significantly down-regulates CD154 transcript expression.

In agreement with previous work (M. Koshy, et al., *J. Clin. Invest.* 98, 826 (1996); A. Desai-Mehta, et al., *J. Clin. Invest.* 97, 2063 (1996)), we find that an increased proportion of SLE T cells express cell-surface CD154 compared to normal and disease controls. To determine if TSA-dependent down-regulation of CD154 mRNA reduces surface expression of CD154, SLE T cells were treated for 18 hr with TSA and the proportion of CD154$^+$ cells quantified by flow cytometry (E. Hagiwara, et al., *Arthritis Rheum.* 39, 379 (1996)). Compared with untreated cells, TSA did not effect any significant reduction of cell-surface CD154$^+$ cells over 24 hr (FIG. 1E). However, activation of SLE T cells with PMA+IO over 24 hr induced a new population of CD154$^+$ cells that was completely inhibited when cells were pretreated with TSA prior to activation (FIG. 1E; P=0.005). By contrast, CD3-ε expression remained stable under these varying conditions, indicating that TSA's effect on CD154 surface expression is not generalized (FIG. 1E). T cells were stained with saturating concentrations of monoclonal FITC-anti-CD3 and PE anti-CD154 antibodies (Caltag Labs, Burlingame, Calif.) for 30 min at 4° C., and the proportion of cells expressing CD3-ε and CD154 was quantified. In sum, these experiments reveal that TSA down-regulates both CD154 mRNA and protein expression, but not GAPDH mRNA or CD3-ε expression, in SLE T cells.

EXAMPLE 2

Down-Regulation of IL-10 Transcript and Protein Levels by TSA

Figure 2:
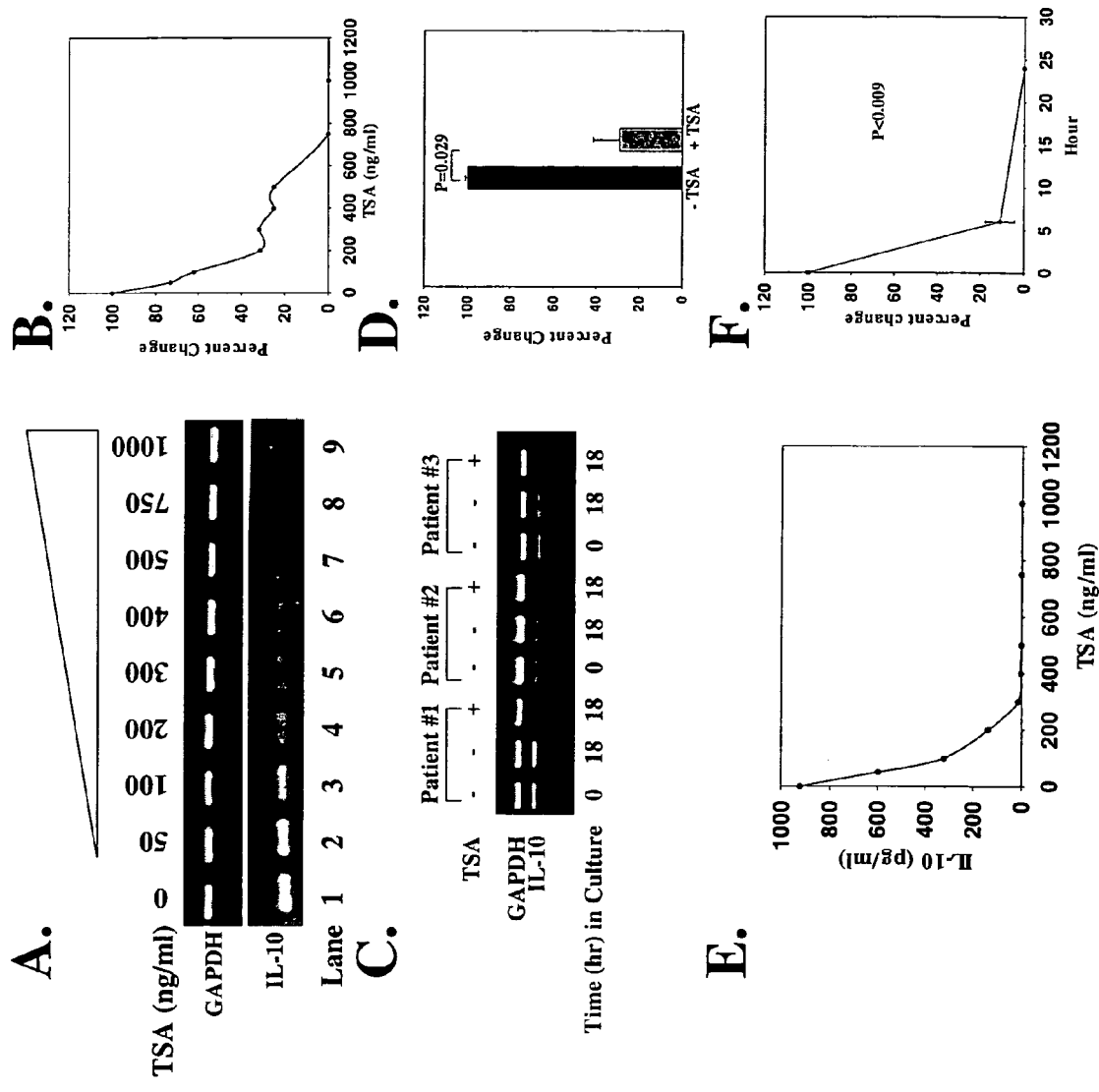
FIG. 2A shows the down-regulation of IL-10 levels by TSA. Increasing concentrations of TSA (0-1000 ng/ml) progressively inhibit expression of IL-10 mRNA relative to expression of GAPDH mRNA.
FIG. 2B shows a graphic depiction of a densitometric scan of the gel in FIG. 2A. This graph depicts the percent change of IL-10 transcript expression with increasing concentrations of TSA over 24 hr.
FIG. 2C shows IL-10 and GAPDH transcripts from T cells of three SLE subjects. Transcripts from freshly isolated T cells are shown in lanes 1, 4, and 7. Transcripts from T cells cultured for 18 hr in the absence or presence of 1000 ng/ml TSA are shown in lanes 2, 5, 8 and 3, 6, and 9, respectively.
FIG. 2D shows a graphic depiction of a densitometric scan of the gel in FIG. 2C. This graph shows the percent change in IL-10 mRNA from SLE T cells cultured in the absence or presence of 1000 ng/ml TSA.
FIG. 2E illustrates the inhibition of IL-10 secretion by increasing concentrations of TSA over 24 hr.
FIG. 2F depicts the percent change of IL-10 production over time. Statistical analysis was performed by paired Student's t test.

T cells from SLE subjects produce markedly increased amounts of IL-10 resulting in high serum levels of the cytokine (B. S. Handwerger, et al., in *Lupus: Molecular and Cellular Pathogenesis*, G. M. Kammer and G. C. Tsokos, Eds. (Humana Press, Totowa, N.J., 1999), chap. 21; E. Hagiwara, et al., *Arthritis Rheum.* 39, 379 (1996)). To determine whether TSA could down-regulate IL-10, a dose-response analysis was performed. Like CD154, increasing concentrations of TSA progressively inhibited IL-10 transcript expression (FIGS. 2A and 2B). In fact, based on sensitive reverse transcriptase-polymerase chain reaction (RT-PCR) analyses, no detectable IL-10 mRNA was identified at TSA concentrations of 700-800 ng/ml. By comparison, increasing concentrations of TSA did not modify GAPDH transcript expression (FIGS. 2A and 2B). As shown in FIG. 2C, IL-10 transcripts were present in freshly isolated T cells (0 hr; lanes 1, 4, 7) and remained stable relative to GAPDH transcripts after culturing cells for 18 hr (lanes 2, 5, 8). However, when SLE T cells were cultured in the presence of TSA for 18 hr, no detectable IL-10 transcripts were identified (FIG. 2C, lanes 3, 6, 9). When IL-10 transcripts from all eight SLE subjects were quantified relative to GAPDH transcripts, TSA inhibited expression of IL-10 mRNA by 71% (FIG. 2D; P=0.029). Treatment of T cells from eight SLE subjects over 18 hr with increasing concentrations of TSA resulted in a dose-dependent inhibition of IL-10 protein production that was maximal at 300 ng/ml of the inhibitor (FIG. 2E). IL-10 and IFN-γ protein production were quantified by ELISA (R & D Systems, Minneapolis, Minn.). Within 6 hr, TSA inhibited IL-10 production by 90%; at 24 hr, there was complete inhibition of IL-10 synthesis (FIG. 2F). Thus, like CD154, TSA was able to block expression of IL-10 transcript, abolishing IL-10 production by SLE T cells.

EXAMPLE 3

UP-Regulation of IFN-γ Transcript and Protein Levels by TSA

Figure 3:
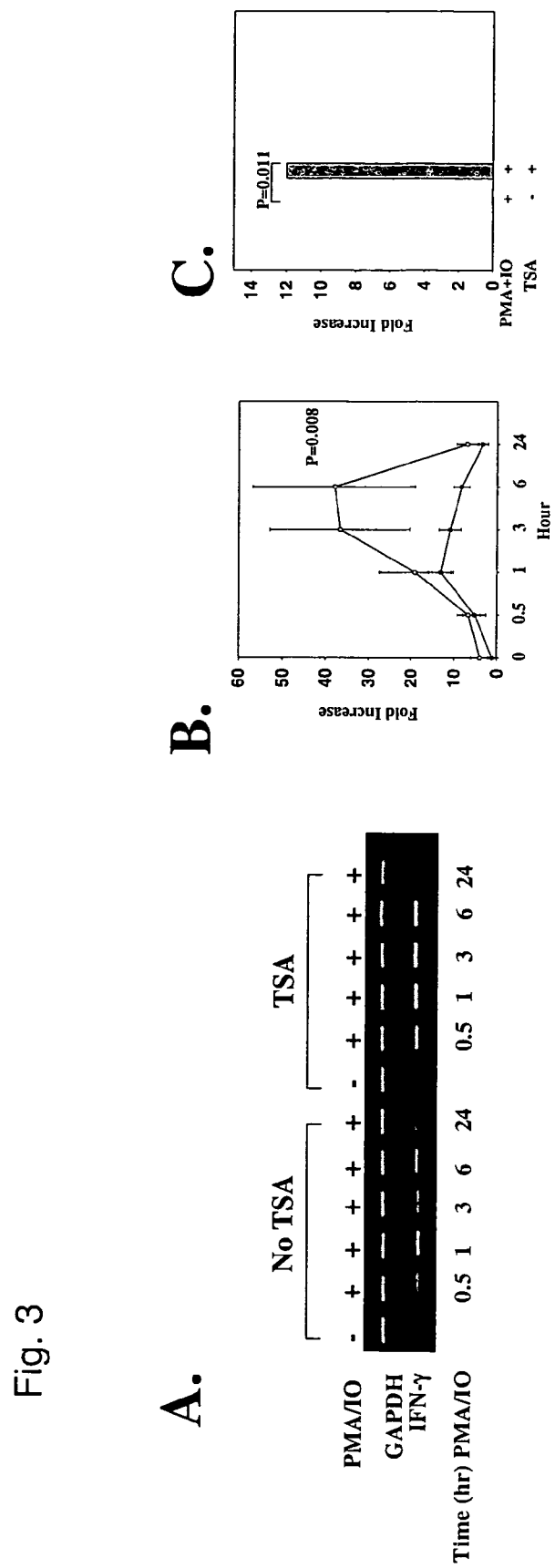
FIG. 3A shows the up-regulation of IFN-γ transcript by TSA. T cells were incubated in the absence or presence of 1000 ng/ml TSA over 18 hr. T cells were then stimulated with 20 ng/ml PMA+0.5 µM IO for intervals to 24 hr. IFN-γ mRNA expression relative to GAPDH mRNA expression is shown.
FIG. 3B shows a graphic depiction of a densitometric scan of the gel in FIG. 3A. This graphs depicts the fold increase of IFN-γ mRNA in cells cultured in the absence (filled circles) or presence (open circles) of 1000 ng/ml TSA during intervals to 24 hr.
FIG. 3C shows IFN-γ protein levels from T cells cultured in the absence or presence of 1000 ng/ml TSA for 24 hr, and then stimulated with 20 ng/ml PMA+0.5 µM IO for 24 hr. The graph shows the fold increase of IFN-γ protein secretion. Statistical analyses were performed by paired Student's t test or one-way ANOVA.

Low production of IFN-γ by SLE T cells may reflect down-regulation of gene expression (B. S. Handwerger, et al., in *Lupus: Molecular and Cellular Pathogenesis*, G. M. Kammer and G. C. Tsokos, Eds. (Humana Press, Totowa, N.J., 1999), chap. 21; E. Hagiwara, et al., *Arthritis Rheum.* 39, 379 (1996)). To establish whether TSA can up-regulate IFN-γ expression, SLE T cells were treated for 18 hr in the absence or presence of TSA. During that time, TSA induced a three-fold increase in IFN-γ transcript compared to untreated cells (FIG. 3A, lanes 1 and 7, and FIG. 3B). When T cells were activated with PMA+IO in the absence of TSA, peak IFN-γ transcript expression increased 13-fold at 1 hr over basal levels relative to GAPDH transcript, but waned thereafter. By contrast, activation of T cells in the presence of TSA induced a peak 37-fold increase in IFN-γ mRNA at 6 hr over untreated cells relative to GAPDH (FIGS. 3A and 3B; P=0.031). Thus, TSA up-regulated expression of IFN-γ transcripts in SLE T cells, yielding both a significantly increased and prolonged expression of the transcript.

This strong up-regulation of IFN-γ transcript was reflected in significantly increased production of IFN-γ protein by 24 hr. In the absence of stimulation, SLE T cells failed to produce any IFN-γ over 72 hr. When T cells were activated with PMA+IO for 24 hr, IFN-γ production increased about 24-fold. However, activation of T cells in the presence of TSA further enhanced IFN-γ output by >12-fold (P=0.011) (FIG. 3C). Taken together, these results demonstrate that TSA rapidly up-regulates both IFN-γ transcript and protein production by SLE T cells.

The capacity of TSA to down-regulate cell surface CD154 and IL-10 production and to up-regulate IFN-γ synthesis in SLE T cells provides new evidence in support of the proposition that skewed gene expression may be a fundamental mechanism underlying both the cellular and humoral immune dysregulation in this disease. That TSA was able to modify this altered gene expression in vitro also supports the concept that HDACs may be recruited to the promoter regions of these genes where they effect skewed expression. Because the precise mechanism by which histone acetylation modifies transcription still remains uncertain (T. Kouzarides, *Curr. Opin. Genet. Dev.* 9, 40 (1999)), it is also unclear how inhibition of HDAC activity by TSA effects down-regulation of CD154 and IL-10 and up-regulation of IFN-γ in SLE T cells. Notwithstanding, this capacity of TSA to modulate the expression of these genes appears to have the salutary effect of normalizing their protein expression in vitro. Because it can simultaneously target multiple genes involved in the immunopathogenesis of lupus, TSA would be an effective therapeutic agent.

In SLE, a chronic inflammatory response progressively destroys organ parenchyma, ultimately leading to irreversible end-organ failure such as end-stage renal disease. The immunopathogenesis of this chronic inflammatory process is in part due to the presence of complement-fixing immune complexes. Formation of pathogenic immune complexes depends on production of autoantibodies, such as anti-native DNA, that arise from dysregulated B cell clones (B. H. Hahn, *New Engl. J. Med.* 338, 1359 (1998)). Therefore, down-regulation of CD154 and IL-10 should eliminate both the sustained CD154-CD40 interaction as well as high cytokine levels that drive polyclonal hypergammaglobulinemia and autoantibody production, reducing immune complex formation. Similarly, up-regulation of IFN-γ production might be expected to normalize an abnormal cellular immune response that predisposes to infections.

The foregoing is illustrative of the present invention, and is not to be construed as limiting thereof. The invention is defined by the following claims, with equivalents of the claims to be included therein.

What is claimed is:

1. A method of treating systemic lupus erythematosus in a subject in need thereof, the method comprising administering to said subject a therapeutically effective amount of suberoylanilide hydroxamic acid or a pharmaceutically acceptable salt thereof, wherein the administering consists of a method of administration selected from the group consisting of oral, parenteral, intramuscular, intravenous, or any combination thereof.

2. A method of treating systemic lupus erythematosus in a subject in need thereof, the method comprising administering to said subject a pharmaceutical formulation comprising a pharmaceutically acceptable carrier and suberoylanilide hydroxamic acid or a pharmaceutically acceptable salt thereof in an amount sufficient to treat a symptom of systemic lupus erythematosus, wherein the administering consists of a method of administration selected from the group consisting of oral, parenteral, intramuscular, intravenous, or any combination thereof.

* * * * *

UNITED STATES PATENT AND TRADEMARK OFFICE
CERTIFICATE OF CORRECTION

| | | |
|---|---|---|
| PATENT NO. | : 7,557,141 B2 | Page 1 of 1 |
| APPLICATION NO. | : 11/403608 | |
| DATED | : July 7, 2009 | |
| INVENTOR(S) | : Mishra et al. | |

It is certified that error appears in the above-identified patent and that said Letters Patent is hereby corrected as shown below:

On the cover, item (62) Related U.S. Application Data:
correct "filed on Nov. 20, 2000, now abandoned"
To read -- filed on Nov. 21, 2000, now abandoned --

Signed and Sealed this
Tenth Day of May, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,557,141 B2 | Page 1 of 1 |
| APPLICATION NO. | : 11/403608 | |
| DATED | : July 7, 2009 | |
| INVENTOR(S) | : Mishra et al. | |

It is certified that error appears in the above-identified patent and that said Letters Patent is hereby corrected as shown below:

In the Specification

Column 1, Lines 13-18: Please delete Statement of Federal Support paragraph and replace with the following:

STATEMENT OF GOVERNMENT SUPPORT
This invention was made with government support under grant number R01 AR039501 awarded by the National Institutes of Health. The government has certain rights in the invention.

Signed and Sealed this
Twenty-third Day of September, 2025

John A. Squires
*Director of the United States Patent and Trademark Office*

```
                       SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1
gaatcctcaa attgcggcac                                                     20

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 2
cagaaggtga cttggcatag                                                     20

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 3
ggtgaaggtc ggagtcaacg                                                     20

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide
```

-continued

```
<400> SEQUENCE: 4
caaagttgtc atggatgacc                                                    20

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 5
ttgcctggtc ctcctgactg                                                    20

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 6
gatgtctggg tcttggttct                                                    20

<210> SEQ ID NO 7
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 7
atgaaatata caagttatat cttggcttt                                          29

<210> SEQ ID NO 8
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 8
gatgctcttc gacctcgaaa cagcat                                             26
```